United States Patent
Wang et al.

(10) Patent No.: US 10,016,734 B2
(45) Date of Patent: Jul. 10, 2018

(54) METHOD OF PRODUCING POTASSIUM SORBATE PARTICLES

(71) Applicant: NINGBO WANGLONG TECH CO.,LTD, Yuyao (CN)

(72) Inventors: Handong Wang, Ningbo (CN); Gongnian Xiao, Ningbo (CN); Guojun Wang, Ningbo (CN); Lijun Chen, Ningbo (CN); Anna Lu, Ningbo (CN); Yuanzhe Chen, Ningbo (CN); Conghui Huang, Ningbo (CN)

( * ) Notice: Subject to any disclaimer, the term of this patent is extended or adjusted under 35 U.S.C. 154(b) by 86 days.

(21) Appl. No.: 15/263,354

(22) Filed: Sep. 12, 2016

(65) Prior Publication Data

US 2018/0028995 A1 Feb. 1, 2018

(30) Foreign Application Priority Data

Jul. 30, 2016 (CN) .......................... 2016 1 0625324

(51) Int. Cl.
*C07C 57/10* (2006.01)
*B01J 2/02* (2006.01)
*B01J 2/16* (2006.01)
*B01J 2/18* (2006.01)

(52) U.S. Cl.
CPC ................ *B01J 2/16* (2013.01); *C07C 57/10* (2013.01)

(58) Field of Classification Search
None
See application file for complete search history.

(56) References Cited

U.S. PATENT DOCUMENTS

| 3,173,948 | A | * | 3/1965 | Probst | ................... | C07C 51/412 |
| | | | | | | 159/48.1 |
| 3,320,307 | A | * | 5/1967 | Kerr | ..................... | C07C 51/412 |
| | | | | | | 562/601 |
| 3,758,563 | A | * | 9/1973 | Uematsu | ............... | A23L 3/3508 |
| | | | | | | 264/115 |
| 4,244,776 | A | * | 1/1981 | Noltner | ................... | C07C 51/43 |
| | | | | | | 159/16.1 |
| 5,946,820 | A | * | 9/1999 | Yoshioka | .................. | B01J 2/00 |
| | | | | | | 34/588 |
| 6,512,142 | B1 | * | 1/2003 | Kouno | .................... | C07C 51/43 |
| | | | | | | 562/601 |

FOREIGN PATENT DOCUMENTS

CN 103351294 * 10/2013

* cited by examiner

*Primary Examiner* — Mary F Theisen
(74) *Attorney, Agent, or Firm* — Wayne & Ken, LLC; Tony Hom

(57) ABSTRACT

The present invention discloses a method of producing potassium sorbate particles, comprising the steps of:

(1) preparing a potassium sorbate solution;
(2) spray drying;
(3) spray forming;
(4) indirectly drying with steam on a vibration fluidized bed; and
(5) swing-type sifting;

in step (3), a binder is obtained by spray drying after adding sorbitol to the potassium sorbate solution prepared in step (1), and the binder is mixed with the potassium sorbate powder obtained by spray drying in step (2) to undergo the spray forming process;

based on weight ratio, the weight ratio of the sorbitol required to prepare the binder to the potassium sorbate solution required to prepare the binder is 0.05-0.1%:1.

The beneficial effects of the present invention are: an appropriate binding effect of the powder particles, a good breaking effect and a good spheronization effect of the powder particles, and uniformity of granulation.

10 Claims, No Drawings

METHOD OF PRODUCING POTASSIUM SORBATE PARTICLES

CROSS-REFERENCE TO RELATED APPLICATIONS

This application claims priority benefit of Chinese Patent Application No. 201610625324.3 with a filing date of Jul. 30, 2016. The content of the aforementioned application, including any intervening amendments thereto, are incorporated herein by reference.

TECHNICAL FIELD

The present invention relates to the field of food additive production, and more particularly, to a method of producing potassium sorbate particles.

BACKGROUND OF THE PRESENT INVENTION

Sorbic acid, also named as Sorbicacid in English, is a kind of unsaturated fatty acid. Sorbic acid is also known as parasorbic acid, 2, 4-hexadienoic acid and 2-propenyl acrylic acid. Sorbic acid is colorless acicular or white powder crystalline, odorless or with slight stimulus odor, light resistant and heat resistant. Potassium sorbate is formed by the chemical reaction between sorbic acid and potassium carbonate which are the raw materials, wherein sorbic acid radical is bonded with potassium ion to form potassium sorbate. Potassium sorbate is white to light yellow flaky crystalline, crystal particle or crystal powder, is odorless or with slight odor, and is easy to absorb moisture and discolor by oxidative decomposition when exposed to air for a long time. Sorbic acid is insoluble in water but is easily soluble in organic solvents such as ethanol, etc., whereas potassium sorbate is very soluble in water as well as in high concentration sucrose and salt solutions, so potassium sorbate is widely used in production. Sorbic acid is an unsaturated acid having 6 carbon atoms. Generally, the commercially available potassium sorbate is white or light yellow particles with a content of 98%-100%. It is odorless or with slight odor, easy to absorb moisture and be oxidized into brown, and stable to light and heat. Its relative density is 1.363, and its melting point is 270° C. with decomposition, and the pH value of the solution with 1% of potassium sorbate is 7-8.

There is a need to develop the powder granulation technique in powder industry production. In different industry fields, powder is often used as an intermediate process of production. But in the production process using powder, there are always many disadvantageous factors such as poor fluidity of powder, difficulties in measurement, dust emission, and difficulties in preservation and transportation, etc. Therefore, the method and process for making powder into particles are applied more and more broadly because of overcoming these disadvantages. Therefore, in order to apply potassium sorbate to various products, it is required to make potassium sorbate into particles.

Chinese patent No. CN103351294A discloses a method of preparing potassium sorbate. The preparation method generally granulates after mixing the dried potassium sorbate powder with potassium sorbate solution during granulation, increasing the binding force, reducing the contact with products by staffs, improving the security of product quality, and making the granulation effect better.

After mixing potassium sorbate powder particles with water, a liquid-bridging force can be formed between particles, but this force is not sufficient to ensure that two powder particles are capable of binding with each other to roll at a high speed. During spheronization, the extruded material will break the powder particles that were bound together originally, while the binding effect of particles will in turn affect the breaking effect of the material. Therefore, there is a need for a method of producing potassium sorbate particles which has the following benefits: an appropriate binding effect of the powder particles, a good breaking effect and a good spheronization effect, and uniformity of granulation.

SUMMARY OF PRESENT INVENTION

The object of present invention is to provide a method of producing potassium sorbate particles which has the following benefits: an appropriate binding effect of the powder particles, a good breaking effect and a good spheronization effect, and uniformity of granulation.

The above technical object of the present invention is achieved by the following technical solutions:

a method of producing potassium sorbate particles, comprising the steps of:
(1) preparing a potassium sorbate solution;
(2) spray drying;
(3) spray forming;
(4) indirectly drying with steam on a vibration fluidized bed; and
(5) swing-type sifting;

in step (3), a binder is obtained by spray drying after adding sorbitol to the potassium sorbate solution prepared in step (1), and the binder is mixed with the potassium sorbate powder obtained by spray drying in step (2) to undergo the spray forming process;

based on weight ratio, the weight ratio of the sorbitol required to prepare the binder to the potassium sorbate solution required to prepare the binder is 0.05-0.1%:1.

Further in the present invention: the amount of the used binder is 10-15% of the weight of the potassium sorbate powder.

Further in the present invention: the drying temperature in step (2) is 200-260° C.

Further in the present invention: the steam temperature in step (4) is 70-95° C.

Further in the present invention: in step (4), the vibration frequency of the vibration fluidized bed is 300-600 r/min, the vibration amplitude is 1-3 mm, and the residence time of the formed potassium sorbate particles is 20-50 s.

Further in the present invention: in step (5), the swing rate is 15-30 Hz.

Further in the present invention: a method of preparing the potassium sorbate solution comprises:

Step1: based on part by weight, adding a water solution with 400-500 parts of potassium carbonate to 1000 parts of crude sorbic acid;

Step2: based on part by weight, adding 45-55 parts of activated carbon, wherein the water temperature is 80-85° C., the reaction time is 35-45 min, and the pH value measured after completion of the reaction is about 8-13; and Step3: after completion of the reaction, adjusting the pH value to 11, stirring for 30 min, and then filtering to obtain the filtered liquid.

Further in the present invention: in Step3, sodium hydroxide is used to adjust the pH value.

Further in the present invention: the mass fraction of potassium carbonate is 55-60%.

Further in the present invention: a method of preparing crude sorbic acid comprises:

S1: based on part by weight, taking and pyrolyzing 700-800 parts of glacial acetic acid to generate ketene gas, then adding 3-16 parts of zinc methacrylate to 600-700 parts of crotonaldehyde and making them react by injecting 150-200 parts of ketene gas at a temperature of 30-40° C. for 4 h;

S2: after completion of the reaction, removing the excess crotonaldehyde by way of reduced pressure distillation, to obtain highly viscous polyester;

S3: based on part by weight, adding 350-400 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 50-100 parts of 65 wt % of ethanol thereto at 60-70° C. and rinsing to obtain crude sorbic acid.

Above all, the present invention yields the following beneficial effects:

1. During granulation, if water is used as a unique binder, the binding effect is limited, which is not beneficial to the spheronization of particles, and if potassium sorbate solution is used alone, it can not achieve a better spheronization effect either. The addition of a small amount of sorbitol is beneficial to the binding and forming effect of particles, and also will not affect the quality of potassium sorbate.

2. The present invention controls the operating conditions of the vibration fluidized bed and improves the drying process of potassium sorbate particles, thus achieving the control of the size of the generated particles.

3. In the present invention, the control of particles is done by way of swing-type sifting, which is beneficial to the control of the size of particles.

DETAILED DESCRIPTION OF PREFERRED EMBODIMENTS

The detailed description is intended to be explanatory only and not restrictive of the invention, and non-innovative modifications can be made to the present invention as needed by persons skilled in the art upon reading the specification. All modifications are under the protection of the Patent Law as long as they fall within the scope of the claims of the present invention.

Embodiments 1-5 are embodiments of preparing crude sorbic acid.

Embodiment 1

S1: based on part by weight, taking and pyrolyzing 700 parts of glacial acetic acid to generate ketene gas, then adding 16 parts of zinc methacrylate to 600 parts of crotonaldehyde and making them react by injecting 200 parts of ketene gas at a temperature of 30° C. for 4 h;

S2: after completion of the reaction, removing the excess crotonaldehyde by way of reduced pressure distillation, to obtain highly viscous polyester;

S3: based on part by weight, adding 350 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 50 parts of 65 wt % of ethanol thereto at 60° C. and rinsing to obtain crude sorbic acid.

Embodiment 2

S1: based on part by weight, taking and pyrolyzing 720 parts of glacial acetic acid to generate ketene gas, then adding 13 parts of zinc methacrylate to 700 parts of crotonaldehyde and making them react by injecting 150 parts of ketene gas at a temperature of 40° C. for 4 h;

S2: after completion of the reaction, removing the excess crotonaldehyde by way of reduced pressure distillation, to obtain highly viscous polyester;

S3: based on part by weight, adding 360 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 75 parts of 65 wt % of ethanol thereto at 70° C. and rinsing to obtain crude sorbic acid.

Embodiment 3

S1: based on part by weight, taking and pyrolyzing 740 parts of glacial acetic acid to generate ketene gas, then adding 10 parts of zinc methacrylate to 620 parts of crotonaldehyde and making them react by injecting 160 parts of ketene gas at a temperature of 33° C. for 4 h;

S2: after completion of the reaction, removing the excess crotonaldehyde by way of reduced pressure distillation, to obtain highly viscous polyester;

S3: based on part by weight, adding 400 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 100 parts of 65 wt % of ethanol thereto at 68° C. and rinsing to obtain crude sorbic acid.

Embodiment 4

S1: based on part by weight, taking and pyrolyzing 760 parts of glacial acetic acid to generate ketene gas, then adding 7 parts of zinc methacrylate to 640 parts of crotonaldehyde and making them react by injecting 170 parts of ketene gas at a temperature of 36° C. for 4 h;

S2: after completion of the reaction, removing the excess crotonaldehyde by way of reduced pressure distillation, to obtain highly viscous polyester;

S3: based on part by weight, adding 370 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 65 parts of 65 wt % of ethanol thereto at 65° C. and rinsing to obtain crude sorbic acid.

Embodiment 5

S1: based on part by weight, taking and pyrolyzing 800 parts of glacial acetic acid to generate ketene gas, then adding 3 parts of zinc methacrylate to 660 parts of crotonaldehyde and making them react by injecting 180 parts of ketene gas at a temperature of 38° C. for 4 h;

S2: after completion of the reaction, removing the excess crotonaldehyde by way of reduced pressure distillation, to obtain highly viscous polyester;

S3: based on part by weight, adding 385 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and S4: filtering under diminished pressure and rinsing with water thereafter to obtain filter cakes, then adding 90 parts of 65 wt % of ethanol thereto at 62° C. and rinsing to obtain crude sorbic acid.

Embodiments 6-10 are embodiments of preparing potassium sorbate particles.

Embodiment 6

The crude sorbic acid used in Embodiment 6 is the crude sorbic acid prepared according to Embodiment 1.

Step1: based on part by weight, adding 1000 parts of crude sorbic acid to a reaction kettle, and then adding water solution, the mass fraction of which is 55%, with 400 parts of potassium carbonate to the reaction kettle, to prepare potassium sorbate water solution;

Step2: based on part by weight, adding 55 parts of activated carbon, wherein the water temperature is 85° C., the reaction time is 35 min, and the pH value measured after completion of the reaction is about 8;

Step3: after completion of the reaction, adjusting the pH value to 11 with sodium hydroxide, stirring for 30 min, and then filtering to obtain the filtered liquid;

Step4: feeding the filtered liquid into a spray dryer via a feeding pump, and drying with hot air at a temperature of 230° C.;

Step5: mixing the potassium sorbate powder obtained after drying with a binder, and spray forming in a forming machine, wherein the binder is obtained by spray drying after adding sorbitol to the potassium sorbate solution obtained in Step3, the weight ratio between the sorbitol and potassium sorbate solution required to prepare the binder is 0.05%:1, and the amount of the used binder is 15% of the weight of the potassium sorbate powder;

Step6: indirectly drying with steam on a vibration fluidized bed, wherein the vibration frequency of the vibration fluidized bed is controlled at 300 r/min, the vibration amplitude is 1 mm, the residence time of the formed potassium sorbate particles is 30 s, and the steam temperature of the vibration fluidized bed is controlled at 95° C.; and Step7: swing-type sifting, wherein the swing rate is controlled at 15 Hz, and the sifting is done with more than 80 meshes.

Embodiment 7

The crude sorbic acid used in Embodiment 7 is the crude sorbic acid prepared according to Embodiment 2.

Step1: based on part by weight, adding 1000 parts of crude sorbic acid to a reaction kettle, and then adding water solution, the mass fraction of which is 56%, with 420 parts of potassium carbonate to the reaction kettle, to prepare potassium sorbate water solution;

Step2: based on part by weight, adding 53 parts of activated carbon, wherein the water temperature is 81° C., the reaction time is 45 min, and the pH value measured after completion of the reaction is about 9;

Step3: after completion of the reaction, adjusting the pH value to 11 with sodium hydroxide, stirring for 30 min, and then filtering to obtain the filtered liquid;

Step4: feeding the filtered liquid into a spray dryer via a feeding pump, and drying with hot air at a temperature of 200° C.;

Step5: mixing the potassium sorbate powder obtained after drying with a binder, and spray forming in a forming machine, wherein the binder is obtained by spray drying after adding sorbitol to the potassium sorbate solution obtained in Step3, the weight ratio between the sorbitol and potassium sorbate solution required to prepare the binder is 0.06%:1, and the amount of the used binder is 14% of the weight of the potassium sorbate powder;

Step6: indirectly drying with steam on a vibration fluidized bed, wherein the vibration frequency of the vibration fluidized bed is controlled at 400 r/min, the vibration amplitude is 2 mm, the residence time of the formed potassium sorbate particles is 50 s, and the steam temperature of the vibration fluidized bed is controlled at 75° C.; and Step7: swing-type sifting, wherein the swing rate is controlled at 17 Hz, and the sifting is done with more than 80 meshes.

Embodiment 8

The crude sorbic acid used in Embodiment 8 is the crude sorbic acid prepared according to Embodiment 3.

Step1: based on part by weight, adding 1000 parts of crude sorbic acid to a reaction kettle, and then adding water solution, the mass fraction of which is 57%, with 440 parts of potassium carbonate to the reaction kettle, to prepare potassium sorbate water solution;

Step2: based on part by weight, adding 50 parts of activated carbon, wherein the water temperature is 82° C., the reaction time is 38 min, and the pH value measured after completion of the reaction is about 10;

Step3: after completion of the reaction, adjusting the pH value to 11 with sodium hydroxide, stirring for 30 min, and then filtering to obtain the filtered liquid;

Step4: feeding the filtered liquid into a spray dryer via a feeding pump, and drying with hot air at a temperature of 250° C.;

Step5: mixing the potassium sorbate powder obtained after drying with a binder, and spray forming in a forming machine, wherein the binder is obtained by spray drying after adding sorbitol to the potassium sorbate solution obtained in Step3, the weight ratio between the sorbitol and potassium sorbate solution required to prepare the binder is 0.07%:1, and the amount of the used binder is 12% of the weight of the potassium sorbate powder;

Step6: indirectly drying with steam on a vibration fluidized bed, wherein the vibration frequency of the vibration fluidized bed is controlled at 450 r/min, the vibration amplitude is 3 mm, the residence time of the formed potassium sorbate particles is 35 s, and the steam temperature of the vibration fluidized bed is controlled at 85° C.; and Step7: swing-type sifting, wherein the swing rate is controlled at 20 Hz, and the sifting is done with more than 80 meshes.

Embodiment 9

The crude sorbic acid used in Embodiment 9 is the crude sorbic acid prepared according to Embodiment 4.

Step1: based on part by weight, adding 1000 parts of crude sorbic acid to a reaction kettle, and then adding water solution, the mass fraction of which is 58%, with 460 parts of potassium carbonate to the reaction kettle, to prepare potassium sorbate water solution;

Step2: based on part by weight, adding 48 parts of activated carbon, wherein the water temperature is 83° C., the reaction time is 40 min, and the pH value measured after completion of the reaction is about 11;

Step3: after completion of the reaction, adjusting the pH value to 11 with sodium hydroxide, stirring for 30 min, and then filtering to obtain the filtered liquid;

Step4: feeding the filtered liquid into a spray dryer via a feeding pump, and drying with hot air at a temperature of 260° C.;

Step5: mixing the potassium sorbate powder obtained after drying with a binder, and spray forming in a forming machine, wherein the binder is obtained by spray drying after adding sorbitol to the potassium sorbate solution obtained in Step3, the weight ratio between the sorbitol and potassium sorbate solution required to prepare the binder is 0.08%:1, and the amount of the used binder is 11% of the weight of the potassium sorbate powder;

Step6: indirectly drying with steam on a vibration fluidized bed, wherein the vibration frequency of the vibration fluidized bed is controlled at 500 r/min, the vibration amplitude is 2 mm, the residence time of the formed potassium sorbate particles is 38 s, and the steam temperature of the vibration fluidized bed is controlled at 80° C.; and Step7: swing-type sifting, wherein the swing rate is controlled at 25 Hz, and the sifting is done with more than 80 meshes.

Embodiment 10

The crude sorbic acid used in Embodiment 10 is the crude sorbic acid prepared according to Embodiment 5.

Step1: based on part by weight, adding 1000 parts of crude sorbic acid to a reaction kettle, and then adding water solution, the mass fraction of which is 60%, with 500 parts of potassium carbonate to the reaction kettle, to prepare potassium sorbate water solution;

Step2: based on part by weight, adding 45 parts of activated carbon, wherein the water temperature is 80° C., the reaction time is 42 min, and the pH value measured after completion of the reaction is about 13;

Step3: after completion of the reaction, adjusting the pH value to 11 with sodium hydroxide, stirring for 30 min, and then filtering to obtain the filtered liquid;

Step4: feeding the filtered liquid into a spray dryer via a feeding pump, and drying with hot air at a temperature of 220° C.;

Step5: mixing the potassium sorbate powder obtained after drying with a binder, and spray forming in a forming machine, wherein the binder is obtained by spray drying after adding sorbitol to the potassium sorbate solution obtained in Step3, the weight ratio between the sorbitol and potassium sorbate solution required to prepare the binder is 0.1%:1, and the amount of the used binder is 10% of the weight of the potassium sorbate powder;

Step6: indirectly drying with steam on a vibration fluidized bed, wherein the vibration frequency of the vibration fluidized bed is controlled at 600 r/min, the vibration amplitude is 3 mm, the residence time of the formed potassium sorbate particles is 20 s, and the steam temperature of the vibration fluidized bed is controlled at 70° C.; and Step7: swing-type sifting, wherein the swing rate is controlled at 30 Hz, and the sifting is done with more than 80 meshes.

Table 1 shows the passage rates with more than 80 meshes of Embodiments 6-10

|  | Embodiment 6 | Embodiment 7 | Embodiment 8 | Embodiment 9 | Embodiment 10 |
| --- | --- | --- | --- | --- | --- |
| passage rates with 80 meshes | 99% | 99% | 100% | 99% | 99% |

Contrast Embodiment 1

Embodiment 1 in Chinese patent No. CN103351294A is selected as Contrast Embodiment 1.

Adding an appropriate amount of water, 1250 kg sorbic acid, 100 kg potassium carbonate and 1180 kg potassium hydroxide to a reaction kettle to neutralize, wherein the pH value is 7.5 and the reaction time is 40 min; after completion of the reaction, adding 20 kg activated carbon and stirring at a temperature of 82° C., and removing the impurities in the solution by adsorption, and then filtering to obtain potassium sorbate; feeding the potassium sorbate into a spray dryer via a feeding pump, and drying with hot air at a temperature of 250° C.; then mixing the above potassium sorbate solution with the dried potassium sorbate powder in a mixer, and keeping the humidity at 7%; granulating in a granulator; indirectly drying the obtained potassium sorbate particles with steam on a fluidized bed, wherein the drying temperature is 80° C.; and swing-type sifting, wherein the swing rate is controlled at 20 Hz, and the sifting is done with more than 80 meshes.

Contrast Embodiment 2

Contrast Embodiment 2 is the same as Embodiment 8 except that the binder in Contrast Embodiment 2 is merely sorbitol, and there is no need for spray drying.

Contrast Embodiment 3

Contrast Embodiment 3 is the same as Embodiment 8 except that sorbitol is removed from the binder in Contrast Embodiment 3.

Contrast Embodiment 4

Contrast Embodiment 4 is the same as Embodiment 8 except that there is no binder in Contrast Embodiment 4.

Table 2 shows the passage rates with more than 80 meshes of Embodiments 8 and Contrast Embodiments 1-4

|  | Embodiment 8 | Contrast Embodiment 1 | Contrast Embodiment 2 | Contrast Embodiment 3 | Contrast Embodiment 4 |
| --- | --- | --- | --- | --- | --- |
| passage rates with 80 meshes | 100% | 75% | 73% | 78% | 65% |

Following Conclusions can be drawn from table 2:

By comparing Embodiment 8 with Contrast Embodiment 1, the passage rate with more than 80 meshes of the potassium sorbate particles generated in the present invention is significantly higher than Contrast Embodiment 1. As seen above, compared with existing technique, the potassium sorbate particles generated in the present invention are more uniform.

By comparing Embodiment 8 with Contrast Embodiments 2-4, the passage rate with more than 80 meshes of the potassium sorbate particles generated in the present invention is significantly higher than Contrast Embodiments 2-4, while the passage rate with more than 80 meshes of the particles generated in Contrast Embodiment 4 is lower than Contrast Embodiments 2-3. As seen above, although potassium sorbate solution and sorbitol are capable of improving the uniformity of granulation in the present invention in different extents, the effect using the binder obtained by mixing potassium sorbate solution and sorbitol to improve the uniformity of granulation will be better than the total effect using potassium sorbate solution and sorbitol to improve the uniformity of granulation respectively. Therefore, the applicants consider that in the present invention, potassium sorbate solution and sorbitol are capable of interacting with each other, improving the uniformity of granulation in the present invention.

We claim:

1. A method of producing potassium sorbate particles, comprising:
   (1) preparing a potassium sorbate solution;
   (2) spray drying the potassium sorbate solution to obtain a potassium sorbate powder;
   (3) mixing a binder with the potassium sorbate powder to produce a mixture and spray forming the mixture in a forming machine to produce the potassium sorbate particles;
   (4) indirectly drying the potassium sorbate particles with steam on a vibration fluidized bed; and
   (5) swing-type sifting the potassium sorbate particles;
   wherein in step (3), the binder is obtained by adding sorbitol to the potassium sorbate solution prepared in step (1) and spray drying the potassium sorbate solution containing sorbitol; and
   the weight ratio of the sorbitol to the potassium sorbate solution in preparing the binder is 0.05-0.1%1.

2. The method of producing potassium sorbate particles of claim 1, wherein the amount of the used binder is 10-15% of the weight of the potassium sorbate powder.

3. The method of producing potassium sorbate particles of claim 1, wherein a drying temperature in step (2) is 200-260° C.

4. The method of producing potassium sorbate particles of claim 1, wherein a steam temperature in step (4) is 70-95° C.

5. The method of producing potassium sorbate particles of claim 1, wherein in step (4), a vibration frequency of the vibration fluidized bed is 300-600 r/min, a vibration amplitude is 1-3 mm, and a residence time of the formed potassium sorbate particles is 20-50 s.

6. The method of producing potassium sorbate particles of claim 1, wherein in step (5), a swing rate is 15-30 Hz.

7. The method of producing potassium sorbate particles of claim 1, wherein a method of preparing the potassium sorbate solution comprises:
   a. based on part by weight, adding a water solution with 400-500 parts of potassium carbonate to 1000 parts of crude sorbic acid;
   b. based on part by weight, adding 45-55 parts of activated carbon, wherein the water temperature is 80-85° C., the reaction time is 35-45 min, and a pH value measured after completion of the reaction is about 8-13; and
   c. after completion of the reaction, adjusting the pH value to 11, stirring for 30 min, and then filtering to obtain the filtered liquid.

8. The method of producing potassium sorbate particles of claim 7, wherein in Step3, sodium hydroxide is used to adjust the pH value.

9. The method of producing potassium sorbate particles of claim 7, wherein the mass fraction of potassium carbonate is 55-60%.

10. The method of producing potassium sorbate particles of claim 7, wherein a method of preparing crude sorbic acid comprises:
   a. based on part by weight, taking and pyrolyzing 700-800 parts of glacial acetic acid to generate ketene gas, then adding 3-16 parts of zinc methacrylate to 600-700 parts of crotonaldehyde and making them react by injecting 150-200 parts of ketene gas at a temperature of 30-40° C. for 4 h;
   b. after completion of the reaction, removing the excess crotonaldehyde by way of reduced pressure distillation, to obtain highly viscous polyester;
   c. based on part by weight, adding 350-400 parts of 23 wt % of concentrated hydrochloric acid to 100 parts of polyester, then heating to 80° C. and aging for 60 min at 75° C. to decompose the polyester, and after which, cooling to 25° C. within 1 h to precipitate crystalline sorbic acid; and
   d. filtering under diminished pressure and rinsing with water thereafter to obtain filter cakes, then adding 50-100 parts of 65 wt % of ethanol thereto at 60-70° C. and rinsing to obtain crude sorbic acid.

* * * * *